(12) United States Patent
Kuang et al.

(10) Patent No.: US 8,940,499 B2
(45) Date of Patent: *Jan. 27, 2015

(54) REAGENT FOR BLOOD ANALYSIS AND METHOD OF USE THEREOF

(75) Inventors: Yuji Kuang, Shenzhen (CN); Baohua Zhang, Shenzhen (CN); Bing Xu, Shenzhen (CN); Jianhui Shao, Shenzhen (CN); Ting Lei, Shenzhen (CN); Li Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 360 days.

This patent is subject to a terminal disclaimer.

(21) Appl. No.: 12/580,474

(22) Filed: Oct. 16, 2009

(65) Prior Publication Data

US 2010/0267080 A1 Oct. 21, 2010

(30) Foreign Application Priority Data

Oct. 17, 2008 (CN) .......................... 2008 1 0216864

(51) Int. Cl.
| | | |
|---|---|---|
| *C07D 215/36* | (2006.01) | |
| *C07D 215/12* | (2006.01) | |
| *C07D 215/14* | (2006.01) | |
| *C07D 215/18* | (2006.01) | |
| *C07D 215/04* | (2006.01) | |
| *C07D 215/10* | (2006.01) | |
| *G01N 33/80* | (2006.01) | |
| *C09K 11/06* | (2006.01) | |
| *G01N 33/50* | (2006.01) | |
| *G01N 33/58* | (2006.01) | |

(52) U.S. Cl.
CPC ................ *G01N 33/80* (2013.01); *C09K 11/06* (2013.01); *G01N 33/5094* (2013.01); *G01N 33/582* (2013.01); *C09K 2211/1011* (2013.01); *C09K 2211/1029* (2013.01); *C09K 2211/1037* (2013.01)
USPC ............. 435/39; 546/172; 546/174; 546/180; 546/181; 546/182

(58) Field of Classification Search
None
See application file for complete search history.

(56) References Cited

U.S. PATENT DOCUMENTS

| | | | |
|---|---|---|---|
| 3,883,247 A | 5/1975 | Adams | |
| 3,883,274 A | 5/1975 | Vuaille | |
| 4,122,348 A | 10/1978 | Bruck | |
| 4,146,604 A | 3/1979 | Kleinerman | |
| 4,286,963 A | 9/1981 | Ledis et al. | |
| 4,325,706 A | 4/1982 | Gershman et al. | |
| 4,332,785 A | 6/1982 | Allen et al. | |
| 4,336,029 A | 6/1982 | Natale | |
| 4,414,325 A | 11/1983 | Masuda et al. | |
| 4,447,547 A | 5/1984 | Allen et al. | |
| 4,485,175 A | 11/1984 | Ledis et al. | |
| 4,528,274 A | 7/1985 | Carter et al. | |
| 4,529,705 A | 7/1985 | Larsen | |
| 4,544,546 A | 10/1985 | Wang et al. | |
| 4,571,388 A | 2/1986 | O'Connell et al. | |
| 4,596,035 A | 6/1986 | Gershman et al. | |
| 4,617,275 A | 10/1986 | Masuda et al. | |
| 4,637,986 A | 1/1987 | Brown et al. | |
| 4,707,451 A | 11/1987 | Sage, Jr. | |
| 4,745,071 A | 5/1988 | Lapicola et al. | |
| 4,751,179 A | 6/1988 | Ledis et al. | |
| 4,822,745 A | 4/1989 | Burns et al. | |

(Continued)

FOREIGN PATENT DOCUMENTS

| | | |
|---|---|---|
| CN | 1101980 | 4/1995 |
| CN | 1101982 | 4/1995 |

(Continued)

OTHER PUBLICATIONS

Mason, SJ. et al. Solid-Phase Catch, Activate, and Release Synthesis of Cyanine Dyes. Organic Letters. 2002, vol. 4(24), p. 4263.*
Fei, X. et al. Solid-Phase Synthesis and Modification of Thiazole Orange and its Derivatives and their Spectral Properties. Journal of Combinatorial Chemistry. 2007, vol. 9(6), p. 945, last two paragraphs.*
U.S. Appl. No. 12/843,671, filed Jul. 26, 2010, Zhao et al.
Notice of Allowance in U.S. Appl. No. 11/967,991 dated Aug. 7, 2009.

(Continued)

*Primary Examiner* — Rita Desai
*Assistant Examiner* — Ben S Michelson
(74) *Attorney, Agent, or Firm* — Kory D. Christensen; Matthew S. Bethards; Stoel Rives LLP (57) ABSTRACT

The present disclosure provides a reagent for blood analysis which may include: (1) a compound having the general formula I as a fluorescent dye, wherein n, X, $R_1$, $R_2$, $R_3$, $R_4$, $R_5$ and $Y^-$ are as defined in the specification; (2) a surfactant selected from cationic surfactants, zwitterionic surfactants and anionic surfactants. The present disclosure also provides a method to perform blood analysis including the following steps of: (a) mixing the blood sample with the reagent for blood analysis disclosed to form a cell suspension; (b) detecting the scattered light signals and fluorescence signals from the cells; and (c) differentiating and counting the cells in the blood in terms of the scattered light signals and fluorescence signals.

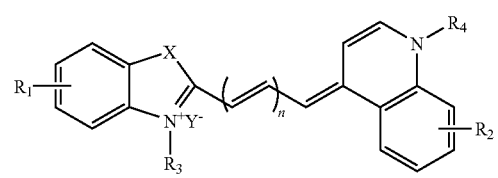

27 Claims, 3 Drawing Sheets

(56) References Cited

U.S. PATENT DOCUMENTS

| | | | |
|---|---|---|---|
| 4,882,284 A | 11/1989 | Kirchanski et al. | |
| 4,883,867 A | 11/1989 | Lee et al. | |
| 4,933,293 A | 6/1990 | Kuroda et al. | |
| 4,957,870 A | 9/1990 | Lee et al. | |
| 4,971,917 A | 11/1990 | Kuroda | |
| 4,978,624 A | 12/1990 | Cremins et al. | |
| 4,981,803 A | 1/1991 | Kuroda | |
| 4,985,174 A | 1/1991 | Kuroda et al. | |
| 5,039,613 A | 8/1991 | Matsuda et al. | |
| 5,075,556 A | 12/1991 | Fan et al. | |
| 5,116,539 A | 5/1992 | Hamaguchi et al. | |
| 5,155,044 A | 10/1992 | Ledis et al. | |
| 5,175,109 A | 12/1992 | Sakata et al. | |
| 5,179,026 A | 1/1993 | Matsuda et al. | |
| 5,180,677 A | 1/1993 | Di Ianni et al. | |
| 5,188,935 A | 2/1993 | Leif et al. | |
| 5,227,304 A | 7/1993 | Wong | |
| 5,232,857 A | 8/1993 | Lefevre et al. | |
| 5,242,832 A | 9/1993 | Sakata | |
| 5,250,437 A | 10/1993 | Toda et al. | |
| 5,264,369 A | 11/1993 | Sakata et al. | |
| 5,284,771 A * | 2/1994 | Fan et al. | 436/10 |
| 5,316,725 A | 5/1994 | Carver et al. | |
| 5,316,951 A | 5/1994 | Carver et al. | |
| 5,321,130 A | 6/1994 | Yue et al. | |
| 5,350,695 A | 9/1994 | Colella et al. | |
| 5,360,739 A | 11/1994 | Fan et al. | |
| 5,389,549 A | 2/1995 | Hamaguchi et al. | |
| 5,411,891 A | 5/1995 | Fan et al. | |
| 5,413,938 A | 5/1995 | Tsujino et al. | |
| 5,438,003 A | 8/1995 | Colella et al. | |
| 5,486,477 A | 1/1996 | Carver et al. | |
| 5,492,833 A | 2/1996 | Rodriguez et al. | |
| 5,496,734 A | 3/1996 | Sakata et al. | |
| 5,510,267 A | 4/1996 | Marshall | |
| 5,516,695 A | 5/1996 | Kim et al. | |
| 5,518,928 A | 5/1996 | Cremins et al. | |
| 5,538,893 A | 7/1996 | Sakata et al. | |
| 5,559,037 A | 9/1996 | Kim et al. | |
| 5,563,070 A | 10/1996 | Yamamoto et al. | |
| 5,616,501 A | 4/1997 | Rodriguez et al. | |
| 5,618,733 A | 4/1997 | Sakata et al. | |
| 5,633,167 A | 5/1997 | Fan et al. | |
| 5,639,630 A | 6/1997 | Malin et al. | |
| 5,639,666 A | 6/1997 | Shenkin | |
| 5,656,449 A | 8/1997 | Yue | |
| 5,677,183 A | 10/1997 | Takarada et al. | |
| 5,686,308 A | 11/1997 | Li et al. | |
| 5,691,204 A | 11/1997 | Kim et al. | |
| 5,731,206 A | 3/1998 | Ledis et al. | |
| 5,733,784 A | 3/1998 | Studholme et al. | |
| 5,747,343 A | 5/1998 | Tsuchiya et al. | |
| 5,763,280 A | 6/1998 | Li et al. | |
| 5,773,299 A | 6/1998 | Kim et al. | |
| 5,786,224 A | 7/1998 | Li et al. | |
| 5,817,518 A | 10/1998 | Li et al. | |
| 5,821,127 A | 10/1998 | Akai et al. | |
| 5,821,128 A | 10/1998 | Provost | |
| 5,840,515 A | 11/1998 | Provost | |
| 5,843,608 A | 12/1998 | Li et al. | |
| 5,858,667 A | 1/1999 | Dertinger et al. | |
| 5,874,311 A | 2/1999 | Li et al. | |
| 5,879,900 A | 3/1999 | Kim et al. | |
| 5,882,934 A | 3/1999 | Li et al. | |
| 5,891,731 A | 4/1999 | Akai et al. | |
| 5,928,949 A | 7/1999 | Sakata et al. | |
| 5,958,776 A | 9/1999 | Sakata et al. | |
| 5,968,832 A | 10/1999 | Uchihashi et al. | |
| 5,994,089 A | 11/1999 | Siiman et al. | |
| 5,994,138 A | 11/1999 | Veriac | |
| 6,004,816 A | 12/1999 | Mizukami et al. | |
| 6,060,322 A | 5/2000 | Horton et al. | |
| 6,100,038 A | 8/2000 | Dertinger et al. | |
| 6,114,130 A | 9/2000 | Veriac et al. | |
| 6,114,173 A | 9/2000 | Zelmanovic et al. | |
| 6,197,593 B1 | 3/2001 | Deka et al. | |
| 6,245,499 B1 | 6/2001 | Suzuki et al. | |
| 6,248,319 B1 * | 6/2001 | Zsebo et al. | 424/85.1 |
| 6,271,035 B1 | 8/2001 | Deka et al. | |
| 6,287,791 B1 | 9/2001 | Terstappen et al. | |
| 6,350,613 B1 | 2/2002 | Wardlaw et al. | |
| 6,368,864 B1 | 4/2002 | Deka et al. | |
| 6,495,692 B1 | 12/2002 | Wang et al. | |
| 6,524,858 B1 | 2/2003 | Zelmanovic et al. | |
| 6,551,831 B2 | 4/2003 | Gupta et al. | |
| RE38,131 E | 6/2003 | Uchihashi et al. | |
| 6,630,990 B2 | 10/2003 | van't Oever et al. | |
| 6,632,676 B1 | 10/2003 | Crews et al. | |
| 6,664,110 B1 | 12/2003 | Tsuji et al. | |
| 6,794,152 B2 | 9/2004 | Ryan et al. | |
| 6,869,798 B2 | 3/2005 | Crews et al. | |
| 6,900,023 B1 | 5/2005 | Houwen et al. | |
| 6,955,872 B2 | 10/2005 | Maples et al. | |
| 6,977,156 B2 | 12/2005 | Ryan et al. | |
| 7,083,982 B2 | 8/2006 | Wang et al. | |
| 7,235,404 B2 | 6/2007 | Lang et al. | |
| 7,247,484 B2 | 7/2007 | Wu et al. | |
| 7,300,797 B2 | 11/2007 | Wenning et al. | |
| 7,405,082 B2 | 7/2008 | Mizukami et al. | |
| 7,449,337 B2 | 11/2008 | Deka et al. | |
| 7,465,584 B2 | 12/2008 | Matsumoto et al. | |
| 7,598,385 B2 | 10/2009 | Peng et al. | |
| 7,709,653 B2 * | 5/2010 | Jianhui | 548/120 |
| 7,960,099 B2 | 6/2011 | Xu et al. | |
| 8,067,602 B2 | 11/2011 | Shao | |
| 8,367,358 B2 | 2/2013 | Ting et al. | |
| 2002/0182623 A1 | 12/2002 | Lefevre et al. | |
| 2003/0145394 A1 | 8/2003 | Wang et al. | |
| 2004/0241769 A1 | 12/2004 | Crews et al. | |
| 2005/0202400 A1 | 9/2005 | Tsuji et al. | |
| 2005/0272026 A1 | 12/2005 | Oguni | |
| 2006/0177347 A1 | 8/2006 | Larsen et al. | |
| 2007/0111276 A1 | 5/2007 | Lefevre et al. | |
| 2007/0178597 A1 | 8/2007 | Tsuji et al. | |
| 2008/0026475 A1 | 1/2008 | van Agthoven et al. | |
| 2008/0131898 A1 | 6/2008 | Tsuji et al. | |
| 2008/0176274 A1 | 7/2008 | Tsuji et al. | |
| 2009/0017441 A1 | 1/2009 | Peng et al. | |
| 2009/0023129 A1 | 1/2009 | Xu et al. | |
| 2009/0176270 A1 | 7/2009 | Shao | |
| 2010/0151509 A1 | 6/2010 | Ting et al. | |
| 2010/0178654 A1 | 7/2010 | Kataoka et al. | |

FOREIGN PATENT DOCUMENTS

| | | |
|---|---|---|
| CN | 1202621 | 12/1998 |
| CN | 1149397 | 5/2004 |
| EP | 0548983 | 6/1993 |
| EP | 0794435 | 9/1997 |
| WO | WO9717471 | 5/1997 |
| WO | WO03104771 | 12/2003 |

OTHER PUBLICATIONS

U.S. Appl. No. 12/482,335, filed Jun. 10, 2009, Shao Jianhui.

U.S. Appl. No. 12/580,474, filed Oct. 16, 2009, Yuji.

Jason A. Bordelon et al., "Viscometry and Atomic Force Microscopy Studies of the Interactions of a Dimeric Cyanine Dye with DNA." J. Phys. Chem. Soc. 2006, 128, pp. 4838-4843.

Alexandre Fuestenburg et al., "Ultrafast Excited-State Dynamics of DNA Fluorescent Intercalators: New Insight into the Fluorescent Enhancement Mechanism." J. Am. Chem. Soc. 2006, 128, pp. 7661-7669.

Kristine M. Slovenhazy et al., "Spectroscopic Studies of the Multiple Binding Modes of a Trimethine-Bridged Cyanine Dye with DNA." Nucleic Acids Research, vol. 31 No. 10, pp. 2561-2569.

L. G. S. Booker et al., "Absorption of Unsymmetrical Carbocyanines." J. Amer. Chem. Soc. 1945, 67, pp. 1889-1893.

Stephen J. Mason et al., "Solid-Phase Catch, Activate, and Release Synthesis of Cyanine Dyes." American Chemical Society Organic Letters 2002, vol. 4 No. 24, pp. 4261-4264.

Notice of Allowance dated Aug. 7, 2009 for U.S. Appl. No. 11/967,991.

(56) References Cited

OTHER PUBLICATIONS

Notice of Allowance in U.S. Appl. No. 11/967,897 dated Feb. 9, 2011.
Notice of Allowance dated Feb. 22, 2010 for U.S. Appl. No. 12/482,335.
Office Action dated Dec. 7, 2011 for U.S. Appl. No. 12/843,671.
Nakamura et al., 'Transition-Metal-Catalyzed Reactions in Heterocyclic Synthesis'. Chem Rev, vol. 104 p. 2127, 2004.
Chattopadhyay et al., 'Formation of Medium-Ring Heterocycles by Diene and Enyne Metathesis'. Tetrahedron vol. 63, p. 3919, 2007.
Dorwold, 'Side Reactions in Organic Synthesis'. Wiley, Preface, 2005.
Netzel, T. et al., "Base-Content Dependence of Emission Enhancements, Quantum Yields, and Lifetimes for Cyanine Dyes Bound to Double Strand DNA: Photophysical Properties of Monomeric and Bichromophoric DNA Stains". 1995, J. Phys. Chem., 99, 17936-179474.
Office Action dated May 10, 2011 for U.S. Appl. No. 12/334,274.
Notice of Allowance in U.S. Appl. No. 11/967,897 dated Mar. 10, 2011.
Notice of Allowance dated Nov. 16, 2012 in U.S. Appl. No. 12/568,500.
Office Action dated Sep. 13, 2013 for U.S. Appl. No. 12/843,671.

* cited by examiner

REAGENT FOR BLOOD ANALYSIS AND METHOD OF USE THEREOF

RELATED APPLICATIONS

This application claims priority to Chinese Patent Application No. 200810216864.1, filed Oct. 17, 2008, for "REAGENT FOR BLOOD ANALYSIS AND METHOD OF USE THEREOF," the disclosure of which is fully incorporated herein by reference.

TECHNICAL FIELD

The present disclosure relates to the field of blood analysis, and more particularly to differentiating and counting cells in the blood.

BRIEF SUMMARY

The present disclosure relates to a reagent for blood analysis and a method of use thereof. More particularly, the present disclosure relates to a reagent for blood analysis useful for differentiating and counting cells in the blood and a method of using said reagent to perform blood analysis.

DETAILED DESCRIPTION

Reticulocytes are cells existing during the transition from the denucleated bone marrow intermediate and late erythroblasts to the fully ripe erythrocytes. Subsequent to their release from bone marrow to peripheral blood, the reticulocytes, as they continue to mature into erythrocytes, show a gradual decrease in RNA content until complete disappearance of RNA in mature erythrocytes. Therefore, the intracellular RNA content represents the maturity of the reticulocytes. The assay of reticulocytes constitutes a fundamental test for evaluating the erythrocyte generation capability in hematological diagnosis and provides a basis for diagnosis of anemia, typing and evaluation of therapeutic efficacy, permitting the determination of the curative effects of chemotherapy and transplantation of bone marrow as well as the therapeutic efficacy of EPO (erythropoietin).

One method currently used for counting reticulocytes is primarily by visual counting under a microscope. However, such a method suffers from the drawbacks of long assay time as well as susceptibility to influences from such factors as staining time, site of observation and skills of the practitioner, and as such it is compromised by a large coefficient of variation and a poor repeatability.

More and more laboratories have started to use a flow cytometer or a fully automatic blood cell analyzer based on the flow cytometry to analyze reticulocytes.

Fluorescent dyes used in early flow cytometry are primarily acridine orange (AO), thioflavin T, chrysaniline and thiazole orange (TO). These dyes have the shortcomings of poor membrane permeability and long incubation time during staining (several minutes to several tens of minutes). The novel fluorescent dye auramine O (AuO) later developed is improved in greatly shortening the time required for staining and incubation (minimum up to 30 seconds). However, the problem of orientational noise associated with this fluorescent dye affects the differentiation and counting of reticulocytes and mature erythrocytes.

Therefore, the present disclosure provides a reagent and a method that allows for rapid and effective differentiation and counting of cells in the blood, such as reticulocytes.

In one aspect of the present disclosure there is provided a reagent for blood analysis which comprises:

(1) A compound having the following general formula I as the fluorescent dye:

I wherein
n is 1, 2 or 3;
X is C(CH$_3$)$_2$, O, S or Se;
R$_1$ and R$_2$ are each independently selected from at least one of following: H, a halogen and C$_{1-18}$alkylsulfonate, provided that R$_1$ and R$_2$ are not all simultaneously H;
R$_3$ and R$_4$ are each independently selected from at least one of the following: C$_{1-18}$alkyl and C$_{1-18}$alkylOR$_5$, provided that R$_3$ and R$_4$ are not simultaneously alkyls when R$_2$ is a halogen;
R$_5$ is hydrogen, acyl or lower alkyl; and
Y$^-$ is an anion; and (2) a surfactant selected from cationic surfactants, zwitterionic surfactants and anionic surfactants.

In another aspect of the present disclosure there is provided a method to perform blood analysis, said method comprising the following steps of: (a) mixing the blood sample with the reagent of the present disclosure to form a cell suspension; (b) detecting the scattered light signals and fluorescence signals from the cells in the cell suspension; and (c) differentiating and counting the cells in the blood in terms of the scattered light signals and fluorescence signals.

The exemplary reagent for blood analysis according to the present disclosure stains excellently and rapidly. The complex formed may have an emission wavelength in the near-infrared region so that interference from the background fluorescence of the organisms per se is avoided and the accuracy of analysis results is improved. It can be used as a staining agent for various biological samples on the flow cytometer.

DEFINITIONS

Unless otherwise specified, the following terms as used herein have the following meanings.

The term "alkyl" as used herein individually or in combination with other groups refers to straight or branched alkyl groups containing 1-18 carbon atoms, such as 1-12, 1-8, and 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The same rules apply to other groups as used throughout the present specification.

As used herein, the term "lower alkyl" has the conventional meaning as used in the art and refers generally to $C_{1-6}$alkyl.

The term "acyl" as used herein refers to "alkyl", as defined above, attached to the group —CO—, wherein said "alkyl" contains 1-18 carbon atoms, such as 1-12, 1-8, and 1-6 carbon atoms, such as formyl, acetyl, and propionyl etc.

The term "halogen" as used herein includes fluorine, chlorine, bromine and iodine.

The term "biological sample" as used herein includes, but is not limited to, nucleic acids, erythroblasts and reticulocytes in the blood.

The Reagent for Blood Analysis According to the Present Disclosure

In one aspect of the present disclosure there is provided a reagent for blood analysis which comprises: (1) a compound having the general formula I as the fluorescent dye; and (2) a surfactant selected from cationic surfactants, zwitterionic surfactants and anionic surfactants.

The Compound Having the General Formula I

Fluorescent dyes commonly used in the prior art are primarily acridine orange (AO), thioflavin T, chrysaniline and thiazole orange (TO). These dyes have the shortcomings of poor membrane permeability and long incubation time from several minutes to several tens of minutes during staining In U.S. Pat. No. 4,981,803 there is disclosed a novel fluorescent dye, auramine O (AuO). This fluorescent dye is improved in shortening the time required for staining and incubation (down to 30 seconds). However, when blood sample is stained with this fluorescent dye, erythrocytes which enter the detection zone may bring the problem of orientational noise affecting the differentiation and counting of reticulocytes and mature erythrocytes.

One compound useful according to the present disclosure as a fluorescent dye has the following general formula I:

wherein
n is 1, 2 or 3;
X is $C(CH_3)_2$, O, S or Se;

$R_1$ and $R_2$ are each independently selected from at least one of the following: H, halogen and $C_{1-18}$alkylsulfonate, provided that $R_1$ and $R_2$ are all not simultaneously H;

$R_3$ and $R_4$ are each independently selected from at least one of the following: $C_{1-18}$alkyl and $C_{1-18}$alkylOR$_5$, provided that $R_3$ and $R_4$ are not simultaneously alkyls when $R_2$ is a halogen;

$R_5$ is hydrogen, acyl or lower alkyl; and

$Y^-$ is an anion.

In one embodiment, $R_1$ and $R_2$ are each independently selected from at least one of the following: H, halogen and $C_{1-6}$alkylsulfonate, provided that $R_1$ and $R_2$ are not simultaneously H.

In one embodiment, $R_3$ is $C_{1-6}$alkyl or $C_{1-6}$alkylOR$_5$.
In one embodiment, $R_4$ is $C_{1-6}$alkyl or $C_{1-6}$alkylOR$_5$.
In one embodiment $R_5$ is H, $C_{1-3}$alkylCO or $C_{1-6}$alkyl.
In one embodiment X is $C(CH_3)_2$, O or S.
In one embodiment n is 1 or 2.

In one embodiment $Y^-$ is selected from halogen ions, $ClO_4^-$, $PF_6^-$, $CF_3SO_3^-$, $B_4^-$, acetate or p-toluenesulfonate anions.

In one embodiment, a compound of formula I is selected from Dye-1, Dye-2, Dye-3, Dye-4, Dye-5, and Dye-6, wherein such dyes have the following structures:

-continued

DYE-6

The compound according to the present disclosure stains biological samples such as nucleic acids, erythroblasts and reticulocytes. The complex formed has an emission wavelength in the near-infrared region so that interference from background fluorescence of the organisms per se may be avoided and the accuracy of analysis results is improved. The compound can be used as staining agent for various biological samples on a flow cytometer.

The compound disclosed herein can be directly used for staining biological samples in the form of salts as described herein. Alternatively, in one embodiment, the compound disclosed herein can exist in the form of derivatives of the compound having the general formula I, said derivatives including, but not limited to, conjugates.

Typically, conjugates are used in a fluorescence activated cell sorter (FACS). "Conjugate" as used herein refers to the compounds formed by attaching the compound disclosed herein to other molecules via covalent bonds. Molecules that can be conjugated with the compound disclosed may be those that specifically bind to cells or cell components, including, but not limited to, antibodies, antigens, receptors, ligands, enzymes, substrates, coenzymes or the like.

Specific description about the compound having the general formula I according to the present disclosure can be found in co-pending Chinese Invention Patent Application No. 200810067815.6 of the present applicant entitled "ASYMMETRIC CYANINE COMPOUNDS, THEIR PREPARATION METHODS AND THEIR USES", which is incorporated herein by reference.

In order that reticulocytes and leukocytes are sufficiently stained, the dye is generally used in a concentration in the range of 1-100 mg/L, such as 5-50 mg/L. Too low a concentration of the dye would result in insufficient staining of cells that, in turn, leads to decrease in the precision of the analysis results. On the contrary, too high a concentration of the dye would increase the background fluorescence from mature erythrocytes. In neither case can the differentiation and counting of reticulocytes be favorably performed.

Surfactants

The reagent for blood analysis according to the present disclosure comprises a surfactant which is selected from cationic surfactants, zwitterionic surfactants and anionic surfactants.

The surfactant contained in the reagent for blood analysis according to the present disclosure can, on the one hand, make mature erythrocytes and reticulocytes sphericized so that the influence of "orientational noise" on analysis is eliminated, and on the other hand, speed up the entry of the dye into the cells so that the intracellular nucleic acids are rapidly stained.

Specific examples of zwitterionic surfactants are cocoamidopropyl betaine and dodecyldimethyl betaine. Zwitterionic surfactants are generally used in a concentration in the range of about 20-150 mg/L.

Specific examples of cationic surfactants are dodecyltrimethylammonium chloride and decyltrimethylammonium chloride. Cationic surfactants are generally used in a concentration in the range of about 50-1200 mg/L.

Specific examples of anionic surfactants are sodium dodecyl sulfate (SDS) and sodium dodecyl benzenesulfonate. Anionic surfactants are generally used in a concentration in the range of about 1-120 mg/L.

Anionic surfactants do not increase the background fluorescence from mature erythrocytes, so reticulocytes are more readily distinguishable from mature erythrocytes. Moreover, use of anionic surfactants provides a clear demarcation of reticulocytes and leukocytes so that better results of differentiation and counting of reticulocytes can be obtained. Therefore, in one embodiment, the surfactant is an anionic surfactant. In another embodiment of the reagent for blood analysis according to the present disclosure, the surfactant is sodium dodecyl sulfate.

Too low a concentration of the surfactant used would result in insufficient sphericization and poor staining of the cells. While too high a concentration of the surfactant used would increase the background fluorescence from mature erythrocytes or even lead to the lysis of erythrocytes.

Other Components

The reagent for blood analysis according to the present disclosure may also comprise a buffering agent for maintaining pH. Common buffering agents such as phosphate, Tris, HEPES and borate can be used alone or in combination in a concentration generally in the range of 0.01-0.1 mmol/L, for example 0.01-0.05 mmol/L. The buffering agent is generally used to maintain the pH value of the reagent according to the present disclosure in the range of 6.0-10.0, such as 7.5-9.5. Too low a pH would decrease the binding capability of the cationic dye to nucleic acids, while too high a pH would increase the background fluorescence from mature erythrocytes.

The reagent for blood analysis according to the present disclosure may also comprise an osmotic regulating agent for regulating osmotic pressure. The osmotic pressure of the reagent according to the present disclosure is typically maintained in the range of 170-350 mOsm/kg, such as 200-350 mOsm/kg. Commonly used alkali metal salts, glucose and mannitol can all maintain the osmotic pressure of the reagent according to the present disclosure in a reasonable range.

Besides the above components, the reagent according to the present disclosure may further comprise a preserving agent selected from parabens and isothiazolinones.

The Method of Using the Reagent for Blood Analysis to Perform Blood Analysis

In another aspect of the present disclosure there is provided a method to perform blood analysis, said method comprising the following steps of: (a) mixing the blood sample with the reagent for blood analysis according to the present disclosure to form a cell suspension; (b) detecting the scattered light signals and fluorescence signals from the cells in the cell suspension; and (c) differentiating and counting the cells in the blood in terms of the scattered light signals and fluorescence signals.

Figure 1:
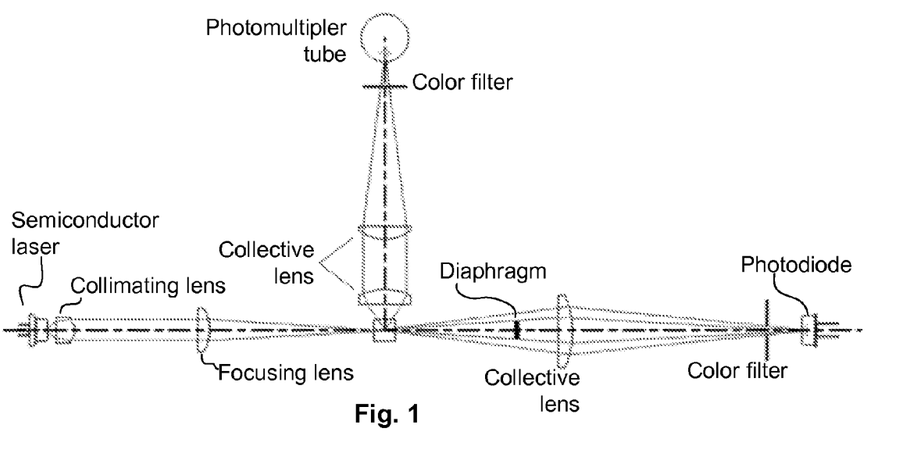
FIG. 1 is a schematic diagram of an exemplary optical system of a flow cytometer used in the analysis method in the examples of the present disclosure.

When performing analysis of blood cells using the reagent for blood analysis according to the present disclosure on the flow cytometer or the fully automatic blood cell analyzer, the blood sample and the reagent for blood analysis according to the present disclosure are first sufficiently mixed in a certain ratio, typically 1:100-1:500, to prepare a homogenous cell suspension, and then the cell suspension is incubated at a reaction temperature of 35-45° C. for 20-40 seconds. Afterwards the cell suspension is injected into the optical system as shown in FIG. 1 for detection.

In the above-said optical system, the individual cells are sequentially passed into the flow chamber and irradiated by the laser whose wavelength is about 630 nm emitted from the semiconductor laser. The fluorescent dye used in the reagent for blood analysis according to the present disclosure is capable of being excited at about 640 nm and its wavelength can remain stable at 40° C., matching the working wavelength of the semiconductor laser used.

Subsequently, the scattered light signals emitted from the cells are collected by the photodiode. The scattered light can be collected at a low angle (0°-5°) or a high angle (6°-20°). The fluorescence signals emitted from the cells are collected by the laterally disposed photomultiplier tube.

Then the scattered light signals and the fluorescence signals are inputted into the data processing unit for analysis. Finally, the various cells in the blood are differentiated and counted in terms of the scattered light signals and fluorescence signals from the cells.

The fluorescent dye used in the reagent of the present disclosure has a certain degree of specific staining capacity for RNA. It is well known that reticulocytes are the precursor cells of mature erythrocytes and contain basophilic substances such as RNA in the cytoplasm. Therefore the reagent of the present disclosure is particularly suited for analyzing reticulocytes in the blood.

EXAMPLES

The present disclosure is further illustrated by the following particular examples to which or by which the present disclosure is not limited.

Unless otherwise stated, the apparatus used in the following examples for analyzing blood cells is the BC series flow cytometer manufactured by Shenzhen Mindray Bio-Medical Electronics Co. Ltd (Shenzhen, People's Republic of China), with the detection wavelength being 640 nm. The schematic diagram of the cell analyzer is as shown in FIG. 1.

Example 1

One example of the reagent for blood analysis according to the present disclosure has the following components:

| | |
|---|---|
| Cyanine dye | 10 mg/L |
| Tris | 2.42 g/L |
| Trisodium citrate•2H$_2$O | 17.64 g/L |
| SDS | 4 mg/L |
| H$_2$O | to a volume of 1 L |

(Adjust the pH value of the reagent to 9.0 with HCl)

Figure 2:
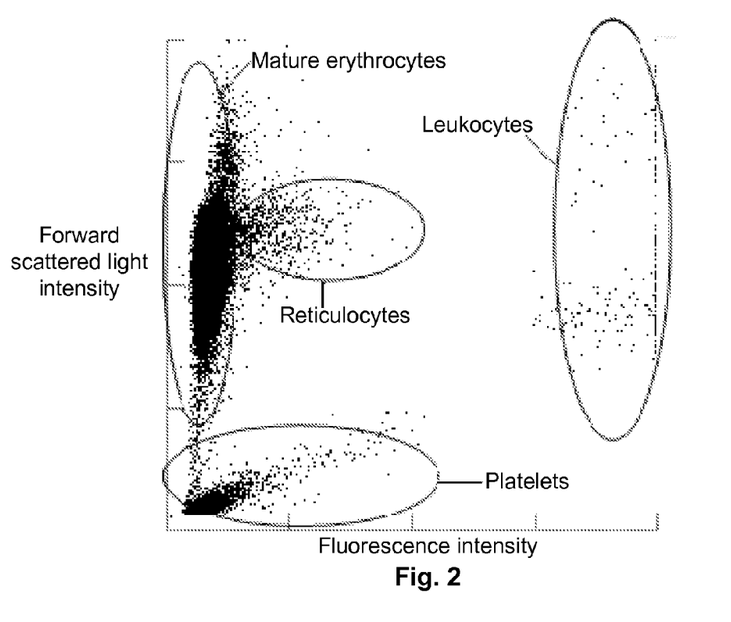
FIG. 2 is a forward scattered light-fluorescence scattergram of a peripheral blood sample measured using the reagent of one example of the present disclosure, comprising fluorescent dye and sodium dodecyl sulfate (SDS).

The cyanine dye used in this example has the following structure:

A blood sample was taken and its reticulocyte content was determined to be 1.60% by the new methylene blue staining method recommended by the International Committee for Standardization of Hematology (ICSH). 4 μL of the blood sample was sufficiently mixed with 1 mL of the above reagent to form a homogenous cell suspension and then the suspension was incubated at 42° C. for 40 seconds. Afterwards the cell suspension was passed through the flow cytometer, and the forward (0°) scattered light signals and fluorescence signals from the cells were detected to generate a scattergram as shown in FIG. 2 in which the reticulocytes accounted for 1.65%.

Example 2

Another example of the reagent for blood analysis according to the present disclosure has the following components:

| | |
|---|---|
| Cyanine dye | 10 mg/L |
| Tris | 2.42 g/L |
| Trisodium citrate•2H$_2$O | 17.64 g/L |
| Decyltrimethylammonium chloride | 800 mg/L |
| H$_2$O | to a volume of 1 L |

(Adjust the pH value of the reagent to 9.0 with HCl)

Figure 3:
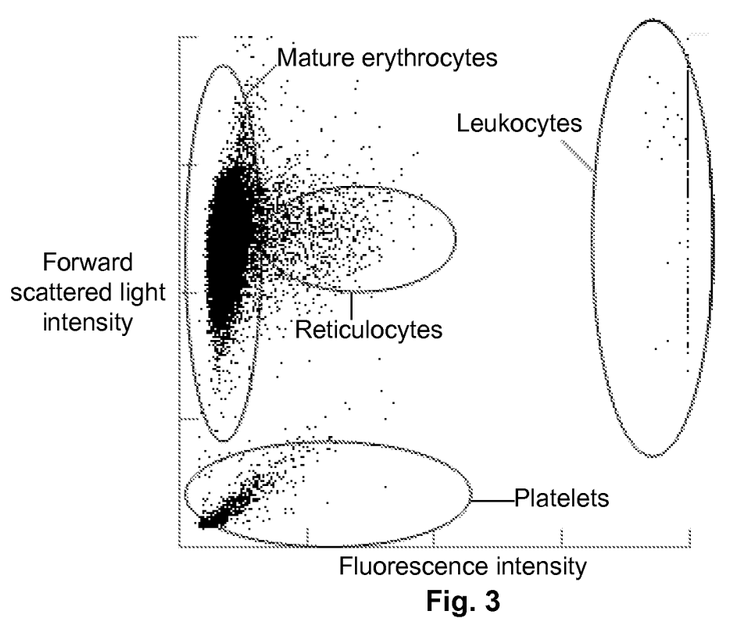
FIG. 3 is a scattergram formed by plotting forward scattered light intensity against fluorescence intensity of peripheral blood measured using the reagent for blood analysis comprising fluorescent dye and decyltrimethylammonium chloride according to another example of the present disclosure.

The cyanine dye used in this example has the following structure:

A blood sample was taken and its reticulocyte content was determined to be 4.10% by the new methylene blue staining method recommended by the International Committee for Standardization of Hematology (ICSH). 4 μL of the blood sample was sufficiently mixed with 1 mL of the above reagent to form a homogeneous cell suspension and then the suspension was incubated at 42° C. for 40 seconds. Afterwards the cell suspension was passed through the flow cytometer, and the forward (0°) scattered light signals and fluorescence signals from the cells were detected to generate a scattergram as shown in FIG. 3 in which the reticulocytes accounted for 4.03%.

Example 3

Yet another example of the reagent for blood analysis according to the present disclosure has the following components:

| | |
|---|---|
| Cyanine dye | 10 mg/L |
| Tris | 2.42 g/L |
| Trisodium citrate•2H$_2$O | 17.64 g/L |
| Cocoamidopropyl betaine | 80 mg/L |
| H$_2$O | to a volume of 1 L |

(Adjust the pH value of the reagent to 9.0 with HCl)

Figure 4:
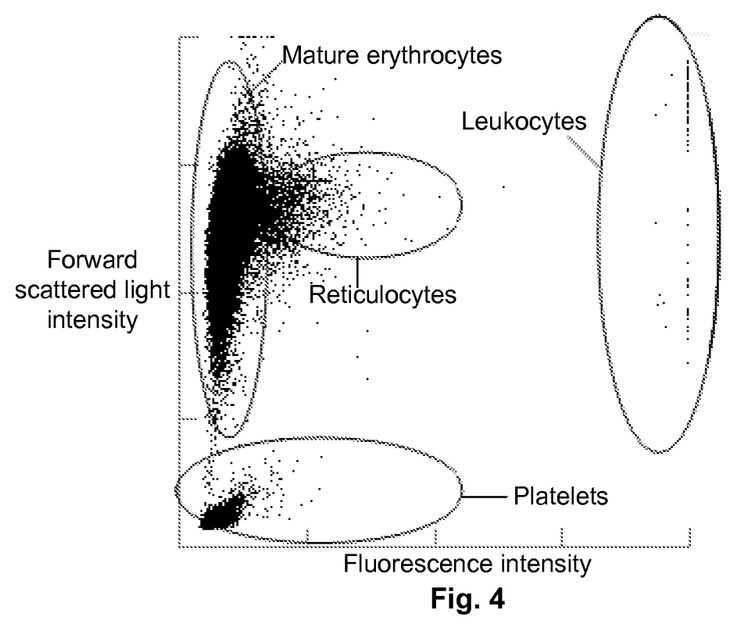
FIG. 4 is a scattergram formed by plotting forward scattered light intensity against fluorescence intensity of peripheral blood measured using the reagent for blood analysis comprising fluorescent dye and cocoamidopropyl betaine according to yet another example of the present disclosure.

The cyanine dye used in this example has the following structure:

A blood sample was taken and its reticulocyte content was determined to be 6.80% by the new methylene blue staining method recommended by the International Committee for Standardization of Hematology (ICSH). 4 μL of the blood sample was sufficiently mixed with 1 mL of the above reagent to form a homogenous cell suspension and then the suspension was incubated at 42° C. for 40 seconds. Afterwards the cell suspension was passed through the flow cytometer and the forward (0°) scattered light signals and fluorescence signals from the cells were detected to generate a scattergram as shown in FIG. 4 in which the reticulocytes accounted for 6.69%.

Example 4

Figure 5:
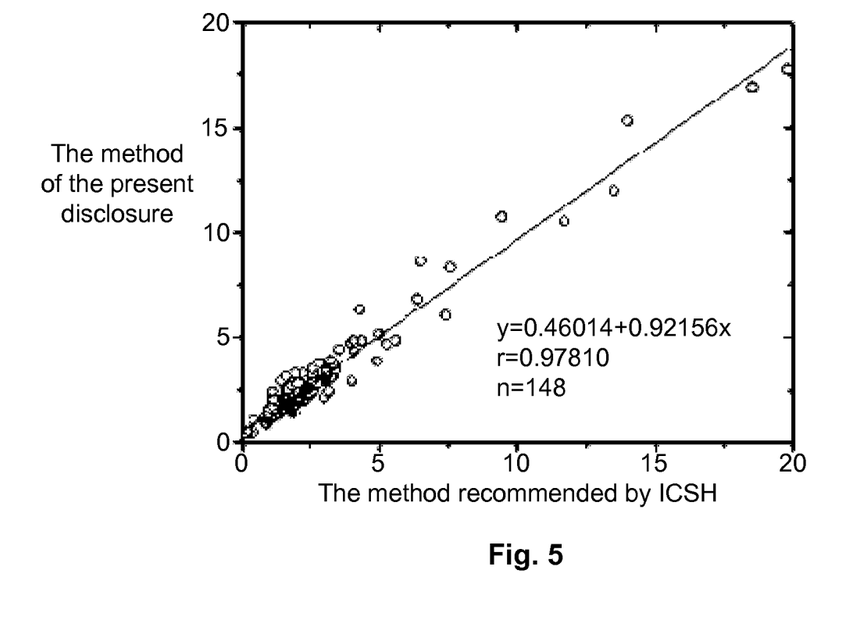
FIG. 5 is a graph which shows the correlation between the measured values of reticulocytes obtained by the analysis method in an example of the present disclosure and those obtained by the new methylene blue staining method recommended by International Committee for Standardization of Hematology (ICSH).

One hundred and forty-eight (148) clinical blood samples were taken, among which 54 samples had normal reticulocytes and 94 samples had abnormal reticulocytes. The reticulocytes in these samples were respectively analyzed by the method as described in Example 1 and the new methylene blue staining method recommended by ICSH. The correlation of the analysis results is as shown in FIG. 5.

It can be seen from the above examples that a rapid and stable analysis of various cells in the blood can be achieved by using the reagent for blood analysis according to the present disclosure.

Although the present disclosure has been illustrated by way of the above embodiments and particular examples thereof, it will be appreciated by those skilled in the art that various changes, alterations and modifications may be made to the present disclosure without departing from the spirit and scope of the present disclosure as defined by the appended claims.

The invention claimed is:

1. A reagent for blood analysis, said reagent comprising:
(1) a compound having the general formula I as the fluorescent dye:

wherein
n is 1, 2 or 3;
X is $C(CH_3)_2$, O, S or Se;
$R_1$ and $R_2$ are each independently selected from at least one of the following: H, halogen and $C_{1-18}$alkylsulfonate, provided that $R_1$ and $R_2$ are not all simultaneously H;
at least one of $R_3$ and $R_4$ is $C_{1-18}$alkylOR$_5$, while the other of $R_3$ and $R_4$ is independently selected from $C_{1-18}$alkyl or $C_{1-18}$alkylOR$_5$;
$R_5$ is hydrogen, acyl or lower alkyl; and
$Y^-$ is an anion; and
(2) a surfactant selected from cationic surfactants, zwitterionic surfactants and anionic surfactants; and
said reagent stains blood cells when incubated for between 20-40 seconds.

2. The reagent for blood analysis according to claim 1, wherein $R_1$ and $R_2$ are each independently selected from at least one of the following: H, halogen and $C_{1-6}$alkylsulfonate, provided that $R_1$ and $R_2$ are not all simultaneously H.

3. The reagent for blood analysis according to claim 1, wherein $R_3$ is $C_{1-6}$alkyl or $C_{1-6}$alkylOR$_5$.

4. The reagent for blood analysis according to claim 1, wherein $R_4$ is $C_{1-6}$alkyl or $C_{1-6}$alkylOR$_5$.

5. The reagent for blood analysis according to claim 1, wherein $R_5$ is H, $C_{1-3}$alkylCO or $C_{1-6}$alkyl.

6. The reagent for blood analysis according to claim 1, wherein X is $C(CH_3)_2$, O or S.

7. The reagent for blood analysis according to claim 1, wherein n is 1 or 2.

8. The reagent for blood analysis according to claim 1, wherein $Y^-$ is selected from halogen ions, $ClO_4^-$, $PF_6^-$, $CF_3SO_3^-$, $BF_4^-$, acetate and p-toluenesulfonate anions.

9. The reagent for blood analysis according to claim 1, wherein the compound having the general formula I is:

or

-continued

10. The reagent for blood analysis according to claim 1, wherein the compound having the general formula I has a concentration in the range of 1 to 100 mg/L.

11. The reagent for blood analysis according to claim 1, wherein the compound having the general formula I has a concentration in the range of 5 to 50 mg/L.

12. The reagent for blood analysis according to claim 1, wherein said surfactant is selected from anionic surfactants.

13. The reagent for blood analysis according to claim 1, wherein said surfactant is selected from zwitterionic surfactants.

14. The reagent for blood analysis according to claim 1, wherein said surfactant is selected from cationic surfactants.

15. The reagent for blood analysis according to claim 1, wherein said surfactant is selected from at least one of the following: sodium dodecyl sulfate, sodium dodecyl benzenesulfonate, cocoamidopropyl betaine, dodecyldimethyl betaine, dodecyltrimethylammonium chloride and decyltrimethylammonium chloride.

16. The reagent for blood analysis according to claim 1, said reagent further comprising a pH buffering agent selected from at least one of the following: phosphate, Tris, HEPES, borate and combinations thereof.

17. The reagent for blood analysis according to claim 16, wherein said pH buffering agent has a pH value in the range of 6.0-10.0.

18. The reagent for blood analysis according to claim 16, wherein said pH buffering agent has a pH value in the range of 7.5-9.5.

19. The reagent for blood analysis according to claim 1, said reagent further comprising an osmotic regulating agent selected from alkali metal salts, glucose or mannitol.

20. The reagent for blood analysis according to claim 19, wherein said osmotic regulating agent maintains the osmotic pressure in the range of 170-350 mOsm/kg.

21. The reagent for blood analysis according to claim 19, wherein said osmotic regulating agent maintains the osmotic pressure in the range of 200-350 mOsm/kg.

22. The reagent for blood analysis according to claim 1, said reagent further comprising a preserving agent selected from parabens and isothiazolinones.

23. A method for blood analysis, said method comprising the following steps of: (a) mixing a blood sample with the reagent for blood analysis according to claim 1 to form a cell suspension; (b) detecting scattered light signals and fluorescence signals from cells in the cell suspension; and (c) differentiating and counting the cells in the blood in terms of the scattered light signals and fluorescence signals.

24. The method according to claim 23, wherein the cells in said step (b) comprise reticulocytes, mature erythrocytes and leukocytes.

25. The method according to claim 24, wherein the cells comprise reticulocytes.

26. The method according to claim 23, wherein the blood sample and the reagent for blood analysis in said step (a) are mixed in a ratio in the range of 1:100 to 1:500.

27. The method according to claim 23, wherein the cell suspension in said step (a) is incubated at a reaction temperature of between 35-45° C. for between 20-40 seconds.

* * * * *